(12) United States Patent
Nowak, Jr.

(10) Patent No.: US 8,403,867 B2
(45) Date of Patent: Mar. 26, 2013

(54) CONCENTRIC GUIDEWIRE ASSEMBLY

(75) Inventor: Thomas Nowak, Jr., North Hampton, NH (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 614 days.

(21) Appl. No.: 12/465,671

(22) Filed: May 14, 2009

(65) Prior Publication Data
US 2010/0292613 A1    Nov. 18, 2010

(51) Int. Cl.
*A61B 5/00*    (2006.01)
(52) U.S. Cl. ........................................................ 600/585
(58) Field of Classification Search ................... 600/585
See application file for complete search history.

(56) References Cited

U.S. PATENT DOCUMENTS

| | | | |
|---|---|---|---|
| 5,830,155 A | 11/1998 | Frechette et al. | |
| 5,891,055 A * | 4/1999 | Sauter | 600/585 |
| 7,322,944 B2 * | 1/2008 | Osawa et al. | 600/585 |
| 7,637,875 B2 * | 12/2009 | Itou | 600/585 |
| 2005/0038359 A1 * | 2/2005 | Aimi et al. | 600/585 |
| 2009/0005706 A1 * | 1/2009 | Miyata et al. | 600/585 |

* cited by examiner

*Primary Examiner* — Max Hindenbrug

(57) ABSTRACT

A concentric guidewire assembly includes a unitary first coil spring, a second coil spring joined to the first coil spring, and a core wire extending through the first and second coil springs. The first coil spring has a longitudinal axis, a first spring portion, a second diameter spring portion adjacent the first spring portion, and a third spring portion adjacent the second spring portion, the inner diameter of the second spring portion being smaller than the inner diameters of the first and third spring portions to fit with the core wire and maintain concentricity between the first coil spring and the core wire. The second coil spring has an inner diameter sized to receive the third spring portion.

9 Claims, 2 Drawing Sheets

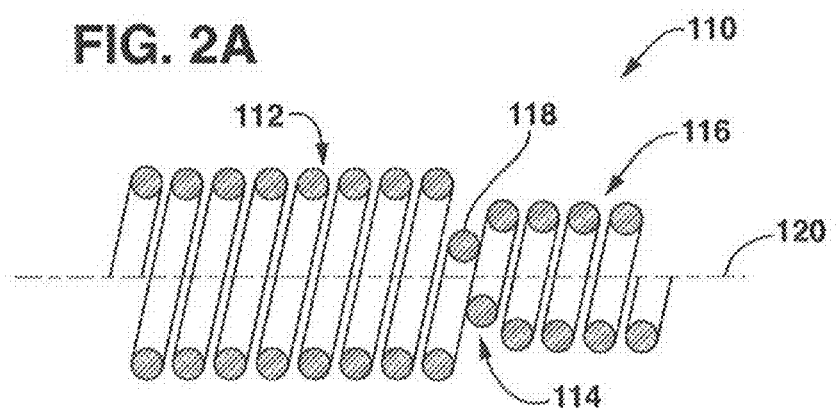
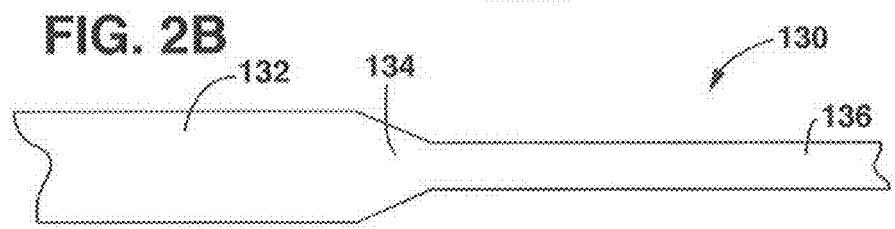
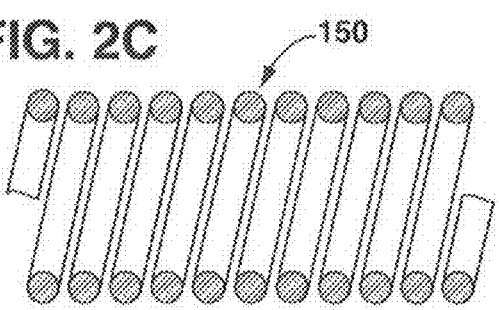
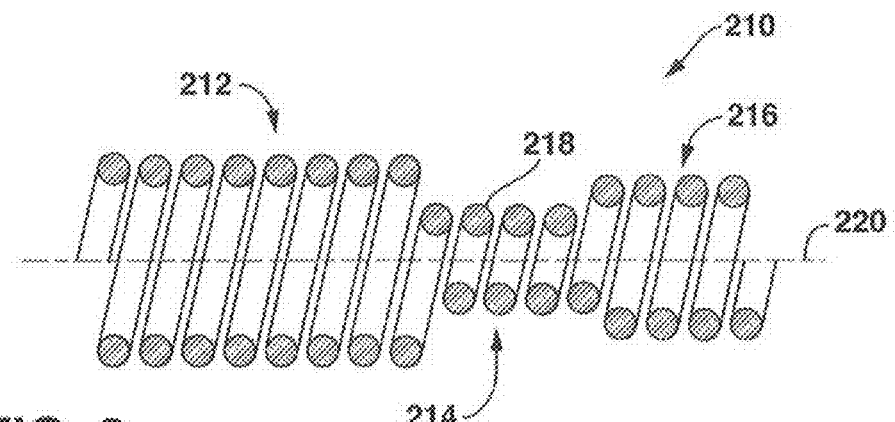

CONCENTRIC GUIDEWIRE ASSEMBLY

TECHNICAL FIELD

The technical field of this disclosure is guidewire assemblies for use in catheterization procedures, particularly, concentric steerable guidewire assemblies.

BACKGROUND OF THE INVENTION

Guidewires are used in catheterization procedures to assist in delivery of treatment devices to the treatment site in the body, such as a blood vessel. A steerable guidewire can be advanced and steered into and along very narrow blood vessels to locate the distal end of the guidewire in a precise position in a selected blood vessel branch. A catheter can then be advanced over the guidewire directly to the desired location in the patient's cardiovascular system to enable the catheter to perform its intended function at that location. For example, the catheter can include a balloon used to dilate the vessel in PTCA (percutaneous transluminal coronary angioplasty) and/or can be used to deliver a stent used to maintain the vessel open.

It is desirable for a steerable guidewire to controllably transmit to the distal end of the guidewire substantially all of the rotation applied at the proximal end, even around tortuous bends in the patient's vasculature. This ideal steerability is sometimes referred to as 1:1 tip torque response. Where a guidewire does not provide 1:1 tip torque response, torsional energy is stored in the guidewire. At some point during arterial insertion the energy may be released causing the guidewire tip to "whip" or move in an unpredictable and uncontrolled manner. For a clinician attempting to navigate a guidewire through tortuous passageways, such unpredictable and uncontrolled behavior is unacceptable.

Steerable guidewires typically include a core wire with a coiled wire spring disposed about the core wire. The symmetrical or central location of the core wire within the spring affects the performance of the guidewire. A guidewire having a non-symmetrical tip such as an off-center core wire may not provide the clinician with the ability to rotationally steer the guidewire without whipping. Unfortunately, the location of the core wire within the spring is not well controlled in present guidewires. Although guidewires are typically illustrated as having the core wire extending along the centerline of the spring, the core wire in the actual fabricated guidewire is typically off-center due to inherent curvature in the core wire or gravity pulling the core wire to one side during assembly. The guidewire steerability suffers because of this asymmetry.

Attempts have been made to center the core wire within the spring by separating the spring into multiple sections or providing additional spacers to center the core wire. Unfortunately, additional sections and spacers increase the complexity of manufacturing the guidewire, increasing assembly time and cost. The additional components can also reduce the flexibility of the guidewire in spots where the additional components are soldered to the spring. It would be desirable to have a concentric guidewire assembly and method of manufacture that would overcome the above disadvantages.

SUMMARY OF THE INVENTION

One aspect of the present invention provides a guidewire assembly with a unitary first coil spring having a longitudinal axis, the unitary first coil spring having a first spring portion, a second spring portion adjacent the first spring portion, and a third spring portion adjacent the second spring portion, the second spring portion having at least one coil concentric about the longitudinal axis; a core wire, the core wire having a first core portion, a tapered portion adjacent the first core portion, and a second core portion adjacent the tapered core portion; and a second coil spring having a diameter sized to receive the third spring portion. The tapered portion is disposed in the second spring portion and the third spring portion is disposed in the second coil spring.

Another aspect of the present invention provides a unitary coil spring having a longitudinal axis, the coil spring including a first spring portion; a second spring portion adjacent the first spring portion; and a third spring portion adjacent the second spring portion. The second spring portion has at least one coil concentric about the longitudinal axis.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

BRIEF DESCRIPTION OF THE DRAWINGS

FIGS. 2A-2C are cross section side views of a concentric guidewire assembly made in accordance with the present invention.

FIG. 3 is a cross section side view of another embodiment of a first spring portion of a concentric guidewire assembly made in accordance with the present invention.

DETAILED DESCRIPTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

Figure 1A:
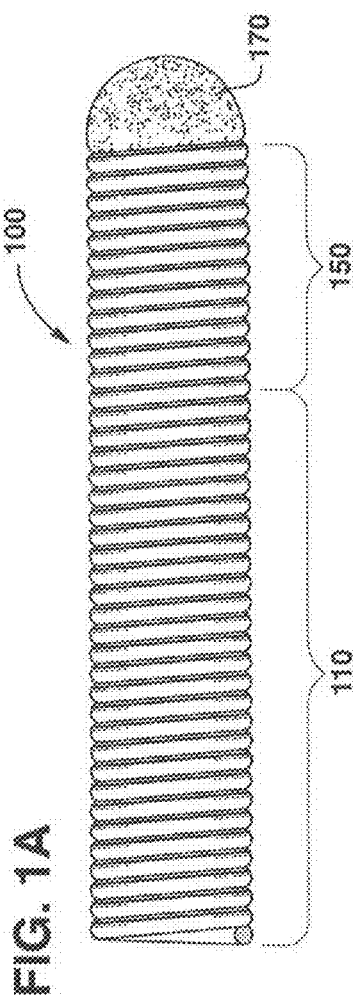
FIGS. 1A & 1B are a side view and cross section side view of a concentric guidewire assembly made in accordance with the present invention.
Figure 1B:
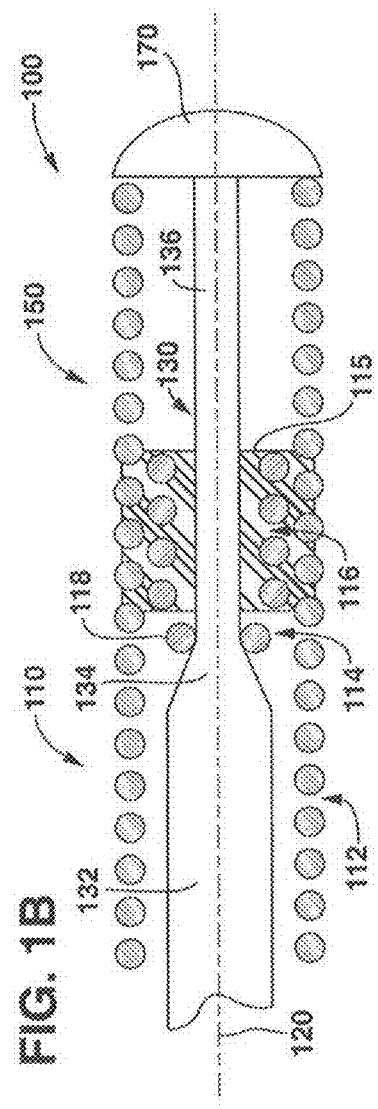

FIGS. 1A & 1B are a side view and cross section side view of a concentric guidewire assembly made in accordance with the present invention. A unitary first coil spring formed from a single wire includes a second spring portion which is concentric about the longitudinal axis of the unitary first coil spring. The second spring portion receives an elongate core wire to locate the core wire concentrically on the axis of the guidewire assembly. The windings or bodies of the springs have been omitted from FIG. 1B for clarity of illustration.

The concentric guidewire assembly 100 includes a unitary first coil spring 110, a core wire 130, and a second coil spring 150. The unitary first coil spring 110 includes a first spring portion 112, a second spring portion 114 adjacent the first spring portion 112, and a third spring portion 116 adjacent the second spring portion 114. The second spring portion 114 has at least one coil 118 concentric about the longitudinal axis 120 of the unitary first coil spring 110. The core wire 130 includes a first core portion 132, a tapered portion 134 adjacent the first core portion 132, and a smaller, second core portion 136 distal of the tapered portion 134. The second coil spring 150 has an outer diameter that is substantially equal to the outer diameter of unitary first coil spring 110 to provide a substantially continuous outer diameter along the entire spring portion of guidewire assembly 100. Second coil spring 150 also has an inner diameter sized to receive and mate with the outer diameter of the third spring portion 116 of the unitary first coil spring 110. The overlapping joint between the inside diameter of second coil spring 150 and the outer diameter of third spring portion 116 may range from a slight clearance fit to an interference fit to achieve concentricity of first coil spring 1110 and second coil spring 150 with core wire 130 and alignment of the outer diameters of first coil spring 110 and second coil spring 150. The core wire tapered portion 134 may be disposed within or at a distance proximal to the second spring portion 114 of the unitary first coil spring 110. A generally hemispherical solder joint or tip 170 can be connected to the second core portion 136 and the second coil spring 150 at the distal end of the concentric guidewire assembly 100.

The second spring portion 114 can be soldered to the core wire 130 at the tapered portion 134 or at a location along second core portion 136. The third spring portion 116 can be fixed between the second coil spring 150 and second core portion 136 by solder 115. In one embodiment, a solderless gap can be maintained between the second spring portion 114 and the third spring portion 116. The solderless gap allows the concentric guidewire assembly 100 to flex at the solderless gap. In another embodiment, no solderless gap is present and the second spring portion 114, third spring portion 116, and second coil spring 150 are connected with a single solder joint that also encloses a portion of core wire 130.

FIGS. 2A-2C, in which like elements share like reference numbers with FIGS. 1A & 1B, are cross section side views of components for a concentric guidewire assembly made in accordance with the present invention. FIGS. 2A-2C are cross section side views of the unitary first coil spring 110, core wire 130, and second coil spring 150, respectively.

The unitary first coil spring 110 is unitary, which is defined herein as being formed from a single wire. The unitary first coil spring 110 and/or second coil spring 150 can be formed with a micro-coiler machine, such as a Kinefac CNC Four Axis Micro-Coiler available from Kinefac® Corporation of Worcester, Mass. In one example, the unitary first coil spring 110 can be formed of stainless steel wire having a wire diameter of 0.002 inch. Second coil spring 150 can be formed of a 0.002 inch diameter radiopaque wire such as platinum tungsten alloy, and be disposed distally of unitary first coil spring 110 to form it concentric, radiopaque-tipped guidewire assembly 100 with an outer diameter of 0.014 inches.

In an alternative embodiment (not shown), coil springs 110 and 150 can be reversed on core wire 130 such that unitary first coil spring 110 can be formed of radiopaque wire and second coil spring 150 can be formed of stainless steel wire and mounted proximally of first coil spring 110 to form a concentric, radiopaque-tipped guidewire assembly 100.

The outer diameter of the first spring portion 112 of the unitary first coil spring 110 can be selected to provide the desired outer diameter for the concentric guidewire assembly 100. The inner diameter of the second spring portion 114 can be selected to mate with the desired portion of core wire 130 to center core wire 130 within first coil spring 110. The joint between the inside diameter of second spring portion 114 and core wire 130 may range from a slight clearance fit to an interference fit to achieve concentricity of the joined components, and may be soldered. The outer diameter of the third spring portion 116 is larger than the outer diameter of second spring portion 114 and can be selected to provide the over-lapping joint described above between the inside diameter of second coil spring 150 and the outer diameter of third spring portion 116. In one embodiment, the pitch and wire diameter of the second coil spring 150 and third spring portion 116 are selected so that the second coil spring 150 can be screwed onto the third spring portion 116. The outer diameter of the second coil spring 150 can be the same as the outer diameter of the first spring portion 112 of the unitary first coil spring 110 to provide a uniform diameter for the concentric guidewire assembly 100. Those skilled in the art will appreciate that the unitary first coil spring 110 can include more or fewer than three portions of different diameters as desired for a particular application.

FIG. 3 is a cross section side view of another embodiment of a first spring portion of a concentric guidewire assembly made in accordance with the present invention. The unitary first coil spring 210 includes a first spring portion 212, a second spring portion 214 adjacent the first spring portion 212, and a third spring portion 216 adjacent the second spring portion 214. The second spring portion 214 has a plurality of coils 218 concentric about the longitudinal axis 220 of the unitary first coil spring 210. In an embodiment of concentric guidewire assembly 100 comprising unitary first coil spring 210, a proximal end portion of second coil spring 150 is disposed over second spring portion 214 and in abutment with the distal end of first spring portion 212 to provide a continuous uniform diameter for the concentric guidewire assembly.

It is important to note that FIGS. 1-3 illustrate specific applications and embodiments of the present invention, and are not intended to limit the scope of the present disclosure or claims to that which is presented therein. Upon reading the specification and reviewing the drawings hereof, it will become immediately obvious to those skilled in the art that myriad other embodiments of the present invention are possible, and that such embodiments are contemplated and fall within the scope of the presently claimed invention.

While the embodiments of the invention disclosed herein are presently considered to be preferred, various changes and modifications can be made without departing from the spirit and scope of the invention. The scope of the invention is indicated in the appended claims, aid all changes that come within the meaning and range of equivalents are intended to be embraced therein.

What is claimed is:

1. A guidewire assembly comprising:
   an elongate core wire;
   a unitary first coil spring having:
      a longitudinal axis;
      a first spring portion having an outer diameter concentric with the longitudinal axis;
      a second spring portion distal of and adjacent to the first spring portion and having at least one coil with an outer diameter smaller than that of the first spring portion and an inner diameter concentric with the longitudinal axis and sized to mate with the core wire; and
      a third spring portion distal of and adjacent to the second spring portion and having an outer diameter larger than that of the second spring portion; and
   a second coil spring having an outer diameter substantially equal to that of the first spring portion and an inner diameter concentric with the longitudinal axis and sized to matingly receive the third spring portion therewithin.

2. The guidewire assembly of claim 1 wherein the at least one coil comprises a plurality of coils.

3. The guidewire assembly of claim 1 wherein the second spring portion is soldered to the core wire and the third spring portion is soldered to the second coil spring.

4. The guidewire assembly of claim 3 further comprising a solderless gap between the second spring portion and the third spring portion.

5. The guidewire assembly of claim 1 wherein the second coil spring is screwed onto the third spring portion.

6. The guidewire assembly of claim 1 wherein the core wire comprises a first core portion, a second core portion distal of and having a smaller diameter than the first core portion and a tapered core portion disposed between the first and second core portions.

7. The guidewire assembly of claim 6 wherein the second spring portion is mated with the tapered core portion.

8. The guidewire assembly of claim 1 wherein the unitary first coil spring is formed of stainless steel wire and the second coil spring is formed of a wire more radiopaque than the stainless steel wire and the second coil spring is disposed distally of the first coil spring to provide a radiopaque-tipped guidewire assembly.

9. The guidewire assembly of claim 1 wherein the second coil spring is formed of stainless steel wire and the unitary first coil spring is formed of a wire more radiopaque than the stainless steel wire and the unitary first coil spring is disposed distally of the second coil spring to provide a radiopaque-tipped guidewire assembly.

* * * * *